US012749187B2

(12) United States Patent
Liu et al.

(10) Patent No.: US 12,749,187 B2
(45) Date of Patent: Sep. 29, 2026

(54) METHOD AND SYSTEM FOR AUTOMATICALLY ESTIMATING MAMMARY GLAND VOLUME BASED ON MAMMARY GLAND MAGNETIC RESONANCE IMAGING (MRI) IMAGE

(71) Applicant: WUHAN UNIVERSITY, Hubei City (CN)

(72) Inventors: Juan Liu, Wuhan City (CN); Haobing Wang, Wuhan City (CN); Jinxuan Hou, Wuhan City (CN)

(73) Assignee: WUHAN UNIVERSITY, Wuhan City (CN)

( * ) Notice: Subject to any disclaimer, the term of this patent is extended or adjusted under 35 U.S.C. 154(b) by 235 days.

(21) Appl. No.: 18/650,449

(22) Filed: Apr. 30, 2024

(65) Prior Publication Data

US 2025/0111504 A1 Apr. 3, 2025

(30) Foreign Application Priority Data

Sep. 28, 2023 (CN) ......................... 202311292822.7

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/13* (2017.01); *G06T 7/136* (2017.01);
(Continued)

(58) Field of Classification Search
CPC ......... G06T 7/0012; G06T 2207/10088; G06T 2207/10092; G06T 2207/10096; G06T 2207/30068; G06T 7/10; G06T 7/11; G06T 7/12; G06T 7/13; G06T 7/136; G06T 7/62; G06T 7/60; G16H 30/20; A61B 6/502;
(Continued)

(56) References Cited

FOREIGN PATENT DOCUMENTS

CN 112184728 A * 1/2021 ............ G06T 7/136

OTHER PUBLICATIONS

Nie K. et al., Development of a quantitative method for analysis of breast density based on three-dimensional breast MRI, 2008, American Association of Physicists in Medicine (Year: 2008).*
(Continued)

*Primary Examiner* — Sumati Lefkowitz
*Assistant Examiner* — Anthony J Rodriguez
(74) *Attorney, Agent, or Firm* — BROOKS KUSHMAN P.C.

(57) ABSTRACT

Provided are a method and system for automatically estimating a mammary gland volume based on a mammary gland magnetic resonance imaging (MRI) image, to automatically segment a mammary gland region in a three-dimensional MRI image of a subject's chest by means of morphological prior knowledge of a breast MRI image and a computer image processing technology, calculate a voxel volume of a segmented part and an actual volume, and guide a doctor in selecting an appropriate fake breast mold. Compared with manual framing of the mammary gland region in conventional practice, the present disclosure can automatically complete marking and volume calculation of the mammary gland region, and greatly improve working efficiency.

18 Claims, 8 Drawing Sheets

(51) Int. Cl.
*G06T 7/13* (2017.01)
*G06T 7/136* (2017.01)
*G06T 7/62* (2017.01)
*G16H 30/20* (2018.01)

(52) U.S. Cl.
CPC ............... *G06T 7/62* (2017.01); *G16H 30/20* (2018.01); *G06T 2207/10088* (2013.01); *G06T 2207/20172* (2013.01); *G06T 2207/20192* (2013.01); *G06T 2207/30068* (2013.01)

(58) Field of Classification Search
CPC ..... A61B 8/0825; A61B 5/0091; A61B 5/708; A61B 2090/063; A61B 5/1073
See application file for complete search history.

(56) References Cited

OTHER PUBLICATIONS

Goodbum R. et al., An automated approach for the optimised estimation of breast density with Dixon methods, 2020, British Institute of Radiology (Year: 2020).*
Espacenet English Translation of CN-112184728-A Description (Year: 2021).*

* cited by examiner

METHOD AND SYSTEM FOR AUTOMATICALLY ESTIMATING MAMMARY GLAND VOLUME BASED ON MAMMARY GLAND MAGNETIC RESONANCE IMAGING (MRI) IMAGE

CROSS-REFERENCE TO RELATED APPLICATIONS

This application claims foreign priority benefits under 35 U.S.C. § 119 (a)-(d) to Chinese patent application No. 202311292822.7, filed on Sep. 28, 2023, the disclosure of which is hereby incorporated herein by reference in its entirety.

TECHNICAL FIELD

The present disclosure relates to the technical field of medical image processing, and in particular, to a method and system for automatically estimating a mammary gland volume based on a mammary gland magnetic resonance imaging (MRI) image.

BACKGROUND

In recent years, the incidence of female breast cancer is becoming increasingly high, which makes breast cancer become one of the most common malignant tumors in women. As a treatment method, mastectomy with a nipple and an areola preserved can not only achieve safety of tumor resection, but also achieve an aesthetic appearance of a breast. In order to achieve symmetry of breasts reconstructed by prostheses, it is very important to choose a prosthesis with a suitable size during an operation, so measurement of a breast related volume before the operation is of great guiding significance for breast reconstruction. There are many methods currently used for measuring a breast volume, such as a formula method, an Archimedes method, a mammary gland X-ray method, a three-dimensional scanning method, and an MRI method. Compared with other methods, the MRI method is the most accurate method to measure a breast volume.

At present, a mainstream method for measuring a breast-related volume by using an MRI image includes the following steps: 1) performing, by a doctor, MRI examination on a patient's chest before an operation, and importing an obtained image into image processing software in a digital imaging and communications in medicine (DICOM) medical image format; 2) parsing the DICOM format by the software, and performing three-dimensional reconstruction on a breast; 3) manually marking, by the doctor, a contour of a mammary gland part in the breast, or manually adjusting upper and lower nuclear magnetic signal thresholds to extract the contour of the mammary gland part; and 4) automatically calculating, by the software, a volume of a mammary gland region according to the obtained mammary gland contour, which is an estimated volume of a breast prosthesis. From this process, it can be seen that the mainstream method relies on manual marking of the mammary gland region, which is time-consuming and laborious in an actual operation, and is prone to an error due to a slice direction problem.

SUMMARY

Against the disadvantages of the prior art, the present disclosure provides a method and system for automatically estimating a mammary gland volume based on a mammary gland MRI image, to automatically extract a mammary gland region from a three-dimensional chest MRI image by means of morphological prior knowledge of a breast MRI image and a computer image processing technology, and estimate a mammary gland volume.

To achieve the above objective, the present disclosure provides a method for automatically estimating a mammary gland volume based on a mammary gland MRI image, including the following steps:

- step 1: reading three-dimensional image data of a chest MRI image in digital imaging and communications in medicine (DICOM) format;
- step 2: cutting the three-dimensional chest MRI image according to prior knowledge to extract a left chest region and a right chest region, and performing Gaussian blur processing on a three-dimensional image of a single breast;
- step 3: removing a breast skin region in the three-dimensional image of the breast by means of an image processing algorithm;
- step 3.1: marking points on an edge of breast skin by means of a probe algorithm;
- step 3.2: calculating partial derivatives of each three-dimensional image of left and right breasts in an X-axis direction, a Y-axis direction, and a Z-axis direction by means of a difference operator, and obtaining a gradient magnitude and direction of a position of each voxel in the three-dimensional image;
- step 3.3: making a mask map based on the points on an edge surface of the breast skin detected in step 3.1, and marking the breast skin region to be eliminated; and
- step 3.4: removing, based on a gradient image obtained in step 3.2, the breast skin region in the three-dimensional image by means of the mask map obtained in step 3.3;
- step 4: processing, by means of an optimized three-dimensional non-maximum suppression algorithm, the three-dimensional image with the breast skin region removed, so as to make a contour of a mammary gland tissue clearer;
- step 5: implementing, in six directions including positive and negative directions of an X-axis, positive and negative directions of a Y-axis, and positive and negative directions of a Z-axis, the probe algorithm on the three-dimensional image subjected to non-maximum suppression, recording all detected edge points to obtain a complete three-dimensional contour of the mammary gland, filling the mammary gland region according to the contour of the mammary gland, and calculating a total number of voxels occupied by the filling to obtain a voxel volume of the mammary gland structure; and
- step 6: calculating a final mammary gland volume according to the voxel volume calculated in step 5 and a voxel spacing.

Moreover, in step 1, data of "t1_f13d_tra_dynaVIEWS_spair_1+6" in a chest MRI image set is read, the data stores three-dimensional images formed by MRI signals in a form of a three-dimensional array, each array element represents one voxel, which is converted into a python array format for storage, and a spacing between voxels in three directions is recorded, where the X-axis is directed from the front to the back of a body, the Y-axis is directed from a left arm to a right arm, and the Z-axis is directed from the top of a head to soles of feet.

Moreover, in step 2, according to prior knowledge on approximate positions of left and right chests in a chest MRI image, the three-dimensional MRI image is cut to extract the left chest region and the right chest region, the right chest region is horizontally flipped according to symmetry of breasts, signals of other organs unrelated to the breasts in the image are cut out to obtain a complete mammary gland region, and the Gaussian blur processing is performed on each three-dimensional image of the left and right breasts obtained through cutting, to eliminate an influence of MRI noise.

Moreover, in step 3.1, samples are taken at intervals in a YZ plane for a three-dimensional image of a single breast subjected to the Gaussian blur processing; for each group of Y and Z, a value of X traverses voxel values one by one in an ascending order, which is equivalent to extending out a probe from the front to the back of the body, and a first voxel point whose voxel value exceeds a preset threshold $\delta$ is marked and recorded, thus obtaining a two-dimensional array in the YZ plane, a first X coordinate of a position of each element that exceeds the threshold $\delta$ is recorded, and the marked voxel points are points on the edge surface of the breast skin.

Moreover, in step 3.2, partial derivative three-dimensional images dx, dy, and dz in the X-axis direction, the Y-axis direction, and the Z-axis direction are first obtained by means of the difference operator from the three-dimensional image of a single breast subjected to the Gaussian blur processing, and then a gradient numerical three-dimensional image is calculated from the three partial derivative images. The difference operator is set as a three-dimensional matrix in which three neighboring voxels in a corresponding direction are −1, 0, and 1, respectively, and the rest values are all 0, and the difference operator of the X-axis, the Y-axis and the Z-axis is expressed as follows:

$$\left(\begin{pmatrix}0&0&0\\0&0&0\\0&0&0\end{pmatrix}\begin{pmatrix}0&0&0\\1&0&-1\\0&0&0\end{pmatrix}\begin{pmatrix}0&0&0\\0&0&0\\0&0&0\end{pmatrix}\right); \tag{1}$$

$$\left(\begin{pmatrix}0&0&0\\0&0&0\\0&0&0\end{pmatrix}\begin{pmatrix}0&1&0\\0&0&0\\0&-1&0\end{pmatrix}\begin{pmatrix}0&0&0\\0&0&0\\0&0&0\end{pmatrix}\right); \text{ and} \tag{2}$$

$$\left(\begin{pmatrix}0&0&0\\0&1&0\\0&0&0\end{pmatrix}\begin{pmatrix}0&0&0\\0&0&0\\0&0&0\end{pmatrix}\begin{pmatrix}0&0&0\\0&-1&0\\0&0&0\end{pmatrix}\right); \tag{3}$$

the gradient numerical three-dimensional image is calculated from the three partial derivative images, and a gradient $\text{Grad}_{i,j,k}$ of a point at a coordinate (i,j,k) is calculated as follows:

$$Grad_{i,j,k} = \sqrt{(A_{i+1,j,k} - A_{i-1,j,k})^2 + (A_{i,j+1,k} - A_{i,j-1,k})^2 + (A_{i,j,k+1} - A_{i,j,k-1})^2} = \sqrt{dx_{i,j,k}^2 + dy_{i,j,k}^2 + dz_{i,j,k}^2}, \tag{4}$$

where A represents a three-dimensional array of the MRI image, i, j, and k represent coordinates, and dx, dy, and dz represent three partial derivative three-dimensional arrays obtained by allowing the difference operator to act on A.

A vector that normalizes three partial derivatives is a direction unit vector of the gradient, and a gradient direction of a position of each voxel marks a direction in which signals increase and decrease fastest, and is orthogonal to a signal equipotential surface of the voxel.

Moreover, in step 3.3, a thickness of the breast skin region is set to K, and the mask map is made based on the points on the edge surface of the breast skin to mark the breast skin region to be eliminated, with a mask calculation formula as follows:

$$y = \frac{\max(\kappa - d, 0)}{\kappa}, \tag{5}$$

where y is a calculated signal value of the mask map, and d represents a distance from a point to the edge surface of the breast skin.

In the mask map, y corresponding to the points on the edge surface of the breast skin is 1, and points at other positions linearly attenuate to 0 with the distance d.

Moreover, in step 3.4, the gradient image of the breast is multiplied by an elimination coefficient $\beta$ to remove the breast skin region in the three-dimensional image.

The elimination coefficient is calculated as follows:

$$\beta = 1 - y, \tag{6}$$

where y is a signal value in the mask map.

Moreover, in step 4, the optimized three-dimensional non-maximum suppression algorithm is calculated by using the following method:

$$U_0 = N_0; \tag{7}$$

$$U_1 = N_1 - U_0; \tag{8}$$

$$U_2 = N_2 - U_0; \tag{9}$$

$$U_3 = N_3 - N_1 - U_2; \tag{10}$$

$$U_4 = N_4 - U_0; \tag{11}$$

$$U_5 = N_5 - N_1 - U_4; \tag{12}$$

$$U_6 = N_6 - N_2 - U_4; \tag{13}$$

$$U_7 = N_7 - N_3 - N_5 + N_1 - U_6; \text{ and} \tag{14}$$

$$R = U_0 + dz \times U_1 + dy(U_2 + dz \times U_3) + dx(U_4 + dz \times U_5) ++ dy(U_6 + dz \times U_7), \tag{15}$$

where $N_0$ to $N_7$ represent voxel values corresponding to 8 octants, dx, dy, and dz are partial derivatives in three directions, and $U_0$ to $U_7$ represent intermediate variables.

A first interpolation $R_1$ is calculated according to the voxel point gradient obtained in step 3.2, then the gradient direction is reversed to select 7 nearest neighboring voxels, a second interpolation $R_2$ is calculated according to formulas (7)-(15), and if the gradient value of the voxel point $N_0$ is greater than $R_1$ and $R_2$, the voxel point is kept, otherwise the voxel value of the voxel point is set to 0.

Moreover, in step 5, a probe extends in the positive direction of the Y-axis to take samples at intervals in an XZ plane; for each group of X and Z, a value of Y traverses voxel values one by one in an ascending order, which is equivalent to extending out the probe from a left arm to a right arm, and a first voxel point whose voxel value exceeds a preset threshold γ is marked and recorded, thus obtaining a two-dimensional array in the XZ plane, and a first Y coordinate at a position of each element that exceeds the threshold γ is recorded. Operations of extending out the probe in five directions including the positive and negative directions of the X-axis, the negative direction of the Y-axis, and the positive and negative direction of the Z-axis are similar to the above operation, edge points detected in all directions are recorded to obtain the complete three-dimensional contour of the mammary gland, the mammary gland region is filled according to the contour of the mammary gland, and the total number of voxels occupied by the filling is calculated to obtain the voxel volume of the mammary gland structure.

The present disclosure further provides a system for automatically estimating a mammary gland volume based on a mammary gland MRI image, which is configured to implement the method for automatically estimating a mammary gland volume based on a mammary gland MRI image described above.

Moreover, the system includes a processor and a memory, where the memory is configured to store program instructions, and the processor is configured to invoke the program instructions in the memory to perform the method for automatically estimating a mammary gland volume based on a mammary gland MRI image described above.

Compared with the prior art, the present disclosure has the following advantages:

1) According to the present disclosure, a computer algorithm is use to process a three-dimensional chest MRI image to automatically obtain an estimated volume of a mammary gland region, which can greatly improve efficiency of a doctor compared with conventional practice that a breast region is manually framed and then a volume is calculated by software.
2) Based on a conventional computer image processing algorithm, the present disclosure can be quickly applied by adjusting model parameters only based on basic prior knowledge such as an MRI image format and a breast position, without the need for any marked samples or any machine learning training.
3) A conventional slice segmentation method is implemented based on a breast slice image, which is likely to cause wrong cutting on upper and lower parts of the breast. According to the present disclosure, the breast image is segmented based on a three-dimensional structure of a breast, which is more suitable for an actual cutting region of a breast surgery, has a smaller system error of mammary gland region segmentation and a larger optimization space, and has more reference value for subsequent breast prosthesis customization.

BRIEF DESCRIPTION OF THE DRAWINGS

To describe the technical solutions in the present disclosure or in the prior art more clearly, the following briefly describes the accompanying drawings required for describing the embodiments or the prior art. Apparently, the accompanying drawings in the following description show some embodiments of the present disclosure, and those skilled in the art may still derive other drawings from these accompanying drawings without creative efforts.

DETAILED DESCRIPTION

To make the objectives, technical solutions and advantages of the present disclosure clearer, the following clearly and completely describes the technical solutions in the present disclosure with reference to the accompanying drawings and embodiments in the present disclosure. Apparently, the described embodiments are some but not all of the embodiments of the present disclosure. All other embodiments obtained by those skilled in the art based on the embodiments of the present disclosure without creative efforts shall fall within the protection scope of the present disclosure.

Embodiment 1

Figure 1:
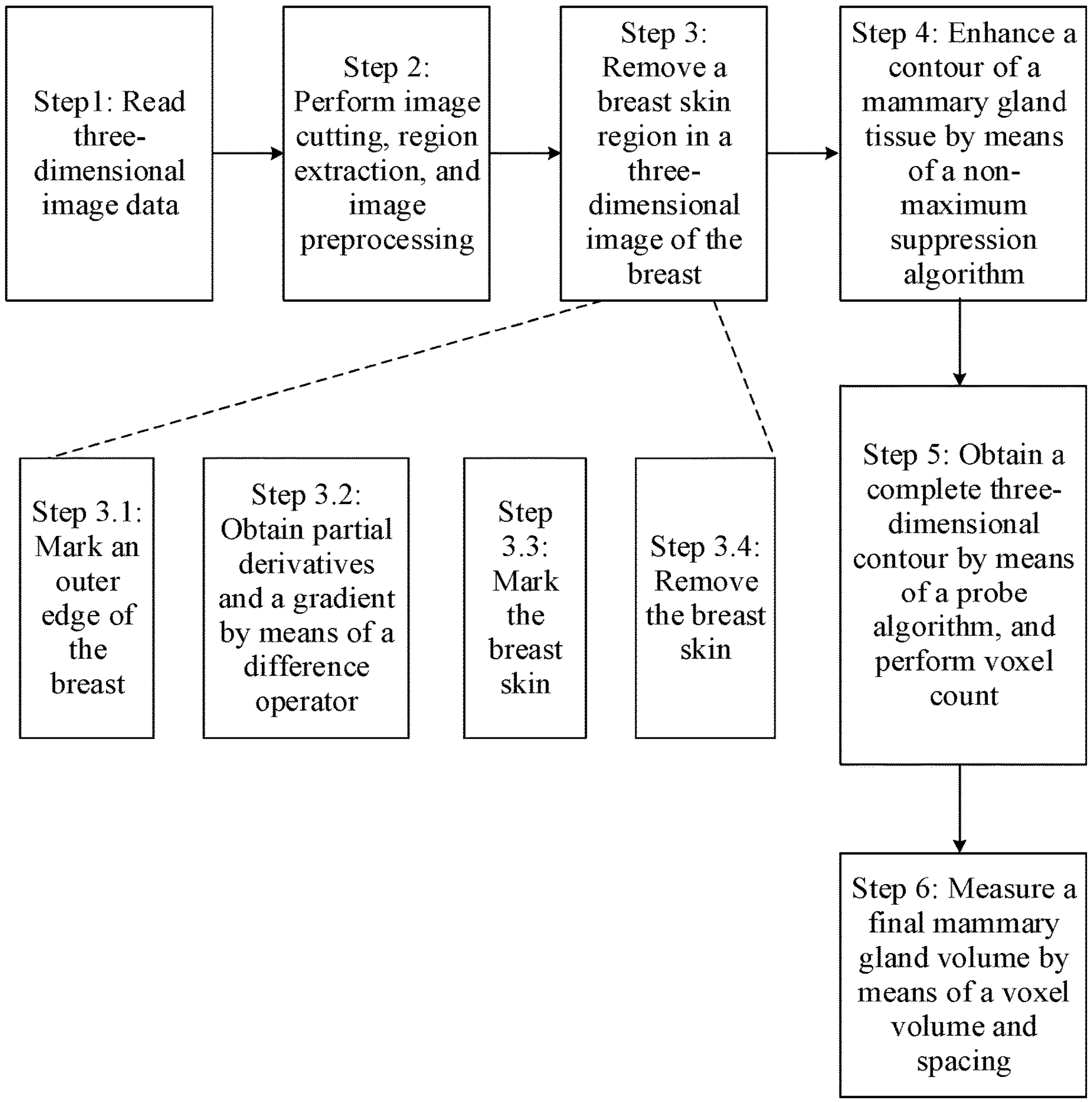
FIG. 1 is a flowchart of a mammary gland volume estimation method according to an embodiment of the present disclosure.

As shown in FIG. 1, an embodiment of the present disclosure provides a method for automatically estimating a mammary gland volume based on a mammary gland MRI image, including the following steps.

Step 1: Read a three-dimensional chest MRI image in DICOM format.

Figure 2:
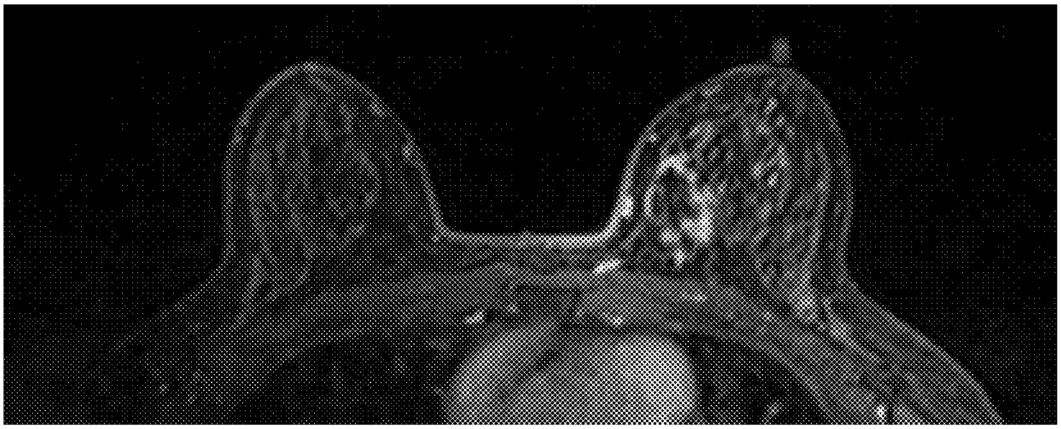
FIG. 2 illustrates a slice of a flipped DICOM format initial image at a right breast nipple position according to an embodiment of the present disclosure, with a subsequent image fixed at this horizontal position to show the slice.

Data of "t1_fl3d_tra_dyna VIEWS_spair_1+6" in a chest MRI image set is read, and the data stores three-dimensional images formed by MRI signals in a form of a three-dimensional array. Each array element represents one voxel, which is converted into a python array format for storage, and a spacing between voxels in three directions is recorded, where the X-axis is directed from the front to the back of a body, the Y-axis is directed from a left arm to a right arm, and the Z-axis is directed from the top of a head to soles of feet. FIG. 2 illustrates a slice in three-dimensional image data of a chest MRI image in DICOM format.

Step 2: Cut the three-dimensional chest MRI image according to prior knowledge to extract a left chest region and a right chest region, and perform Gaussian blur processing on a three-dimensional image of a single breast.

Figure 3:
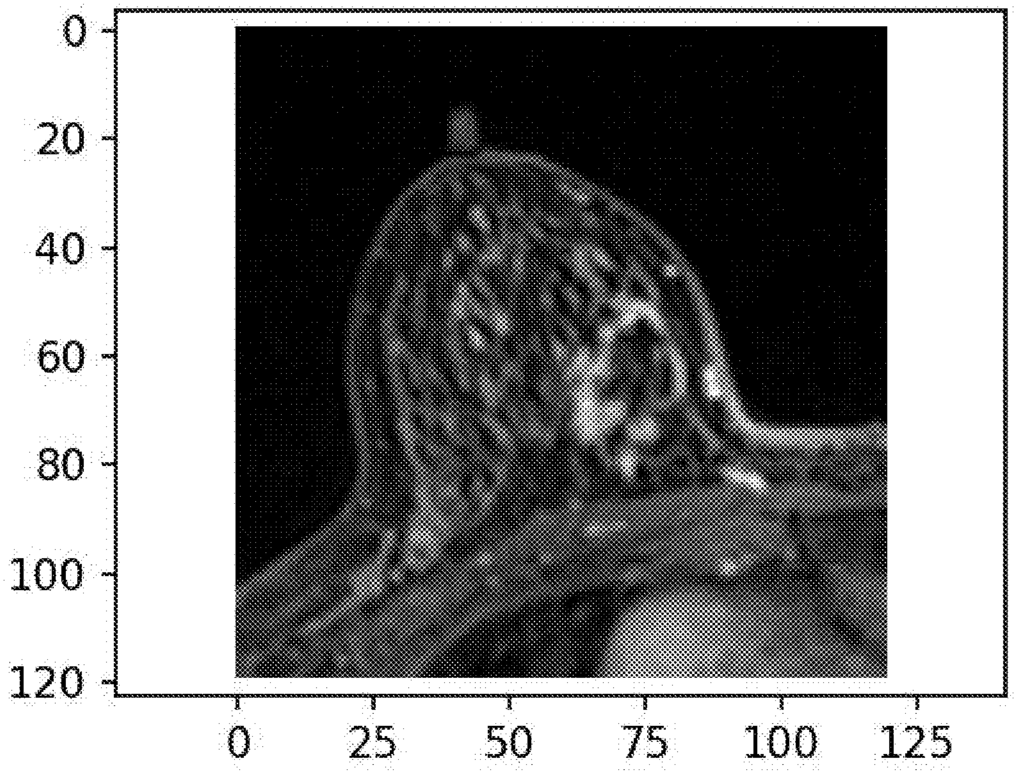
FIG. 3 is a cut right breast part patch according to an embodiment of the present disclosure.

According to a convention of photographing an MRI image, the range of positions of left and right chest slices is shown in Table 1. According to prior knowledge on approximate positions of left and right chests in a chest MRI image, the obtained three-dimensional image is cut to extract the left chest region and the right chest region, the right chest region is horizontally flipped according to symmetry of breasts, so that regions and main line slopes of the left and right breasts in the image are approximately the same, and signals of other organs unrelated to the breasts in the image are cut out to obtain a complete mammary gland region. The cut three-dimensional image of the right breast is shown in FIG. 3.

TABLE 1

| Position range of left and right chest slices | | | |
|---|---|---|---|
| | X | Y (right chest flipped) | Z |
| Left chest | 80-200 | 56-176 | 0-111 |
| Right chest | 80-200 | 296-176 | 0-111 |

Figure 4:
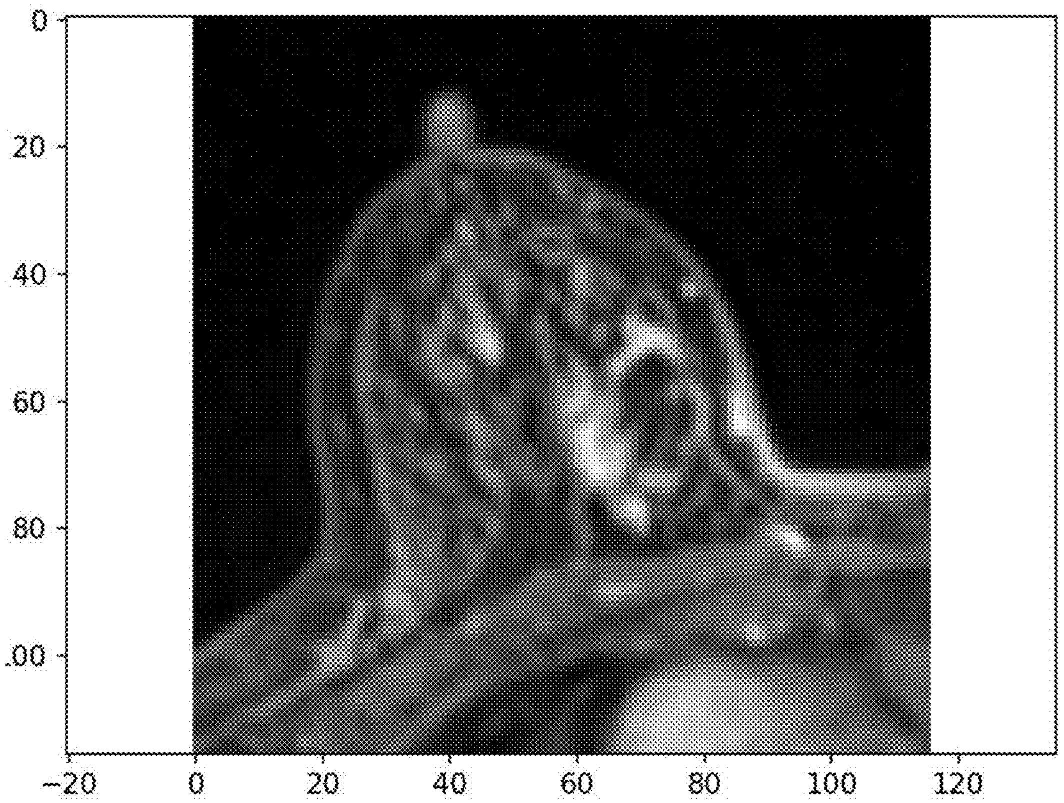
FIG. 4 is a right breast part patch subjected to Gaussian blur according to an embodiment of the present disclosure.

Gaussian blur processing is performed on each three-dimensional image of the left and right breasts, to eliminate an influence of MRI noise. In this embodiment, a mean value of a Gaussian convolution kernel is 5, and a variance value is 1.5. A result of Gaussian blur processing is shown in FIG. 4.

Step 3: Remove a breast skin region in the three-dimensional image of the breast by means of an image processing algorithm.

Step 3.1: Mark points on an edge of breast skin by means of a probe algorithm.

Figure 5:
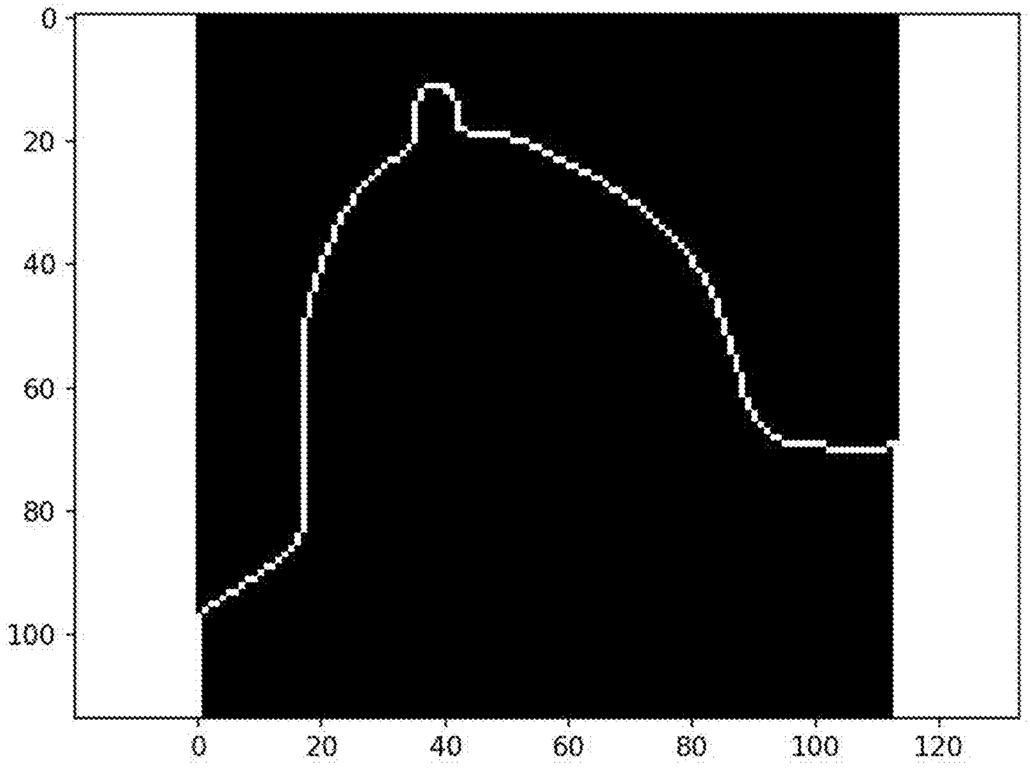
FIG. 5 is an outer edge image of a right breast according to an embodiment of the present disclosure.

Samples are taken at intervals in a YZ plane for a three-dimensional image of a single breast subjected to the Gaussian blur processing; for each group of Y and Z, a value of X traverses voxel values one by one in an ascending order (which is equivalent to extending out a probe from the front to the back of the body), and a first voxel point whose voxel value exceeds a preset threshold δ is marked and recorded. Therefore, a two-dimensional array in the YZ plane can be obtained, and a first X coordinate of a position of each element that exceeds the threshold δ is recorded. The marked voxel points are points on the edge surface of the breast skin. In this embodiment, according to practical experience, the threshold δ is set to 25, a sampling interval in the YZ plane is 0, and an identified breast skin edge is shown in FIG. 5.

Step 3.2: Calculate partial derivatives of each three-dimensional image of left and right breasts in an X-axis direction, a Y-axis direction, and a Z-axis direction by means of a difference operator, and obtain a gradient magnitude and direction of a position of each voxel in the three-dimensional image.

Partial derivative three-dimensional images dx, dy, and dz in the X-axis direction, the Y-axis direction, and the Z-axis direction are first obtained by means of the difference operator from the three-dimensional image of a single breast subjected to the Gaussian blur processing, and then a gradient numerical three-dimensional image is calculated from the three partial derivative images. The difference operator is set as a three-dimensional matrix in which three neighboring voxels in a corresponding direction are −1, 0, and 1, respectively, and the rest values are all 0, and the difference operator of the X-axis, the Y-axis and the Z-axis may be expressed as follows:

$$\left(\begin{pmatrix}0&0&0\\0&0&0\\0&0&0\end{pmatrix}\begin{pmatrix}0&0&0\\1&0&-1\\0&0&0\end{pmatrix}\begin{pmatrix}0&0&0\\0&0&0\\0&0&0\end{pmatrix}\right); \tag{1}$$

-continued $$\left(\begin{pmatrix}0&0&0\\0&0&0\\0&0&0\end{pmatrix}\begin{pmatrix}0&1&0\\0&0&0\\0&-1&0\end{pmatrix}\begin{pmatrix}0&0&0\\0&0&0\\0&0&0\end{pmatrix}\right); \text{ and} \tag{2}$$

$$\left(\begin{pmatrix}0&0&0\\0&1&0\\0&0&0\end{pmatrix}\begin{pmatrix}0&0&0\\0&0&0\\0&0&0\end{pmatrix}\begin{pmatrix}0&0&0\\0&-1&0\\0&0&0\end{pmatrix}\right); \text{ and} \tag{3}$$

the gradient numerical three-dimensional image is calculated from the three partial derivative images, and a gradient $Grad_{i,j,k}$ of a point at a coordinate (i,j,k) is calculated as follows:

$$Grad_{i,j,k} = \sqrt{(A_{i+1,j,k}-A_{i-1,j,k})^2+(A_{i,j+1,k}-A_{i,j-1,k})^2+(A_{i,j,k+1}-A_{i,j,k-1})^2} = \sqrt{dx_{i,j,k}^2+dy_{i,j,k}^2+dz_{i,j,k}^2}, \tag{4}$$

where A represents a three-dimensional array of the MRI image, i, j, and k represent coordinates, and dx, dy, and dz represent three partial derivative three-dimensional arrays obtained by allowing the difference operator to act on A.

Figure 6:
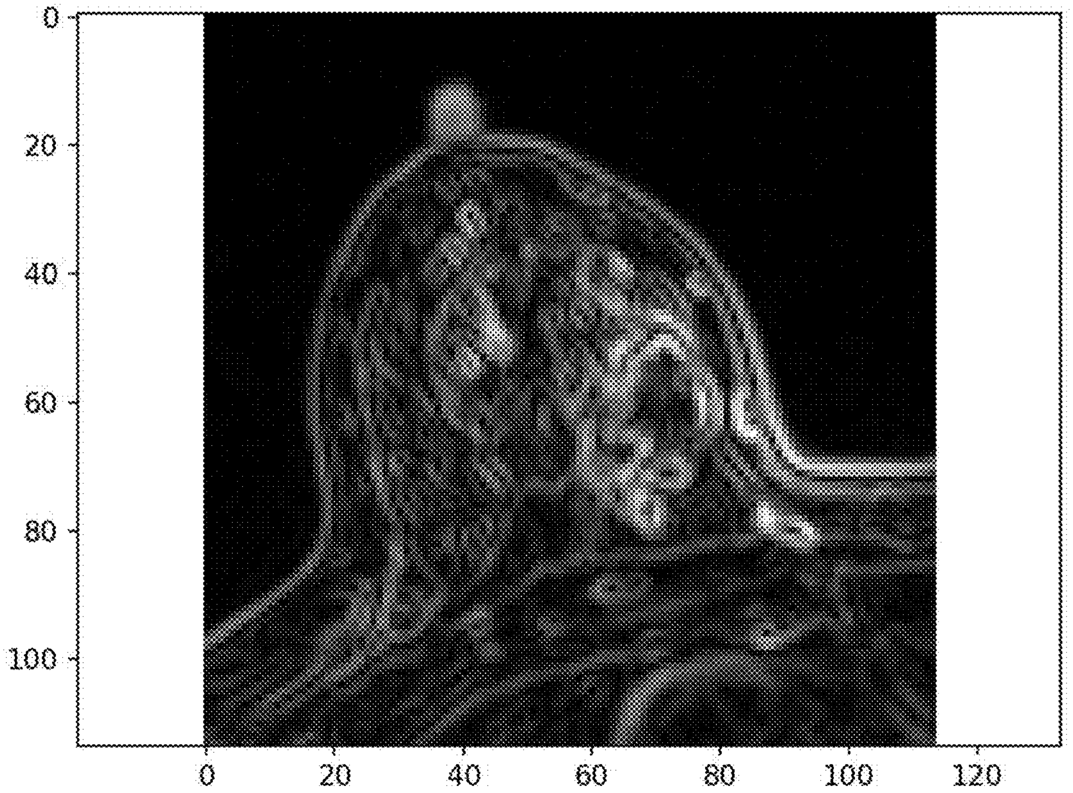
FIG. 6 is a gradient image of a right breast according to an embodiment of the present disclosure.

A vector that normalizes three partial derivatives is a direction unit vector of the gradient, and a gradient direction of a position of each voxel marks a direction in which signals increase and decrease fastest, and is orthogonal to a signal equipotential surface of the voxel. A final gradient image of the right breast is shown in FIG. 6.

Step 3.3: Make a mask map based on the points on an edge surface of the breast skin detected in step 3.1, and mark the breast skin region to be eliminated.

Figure 7:
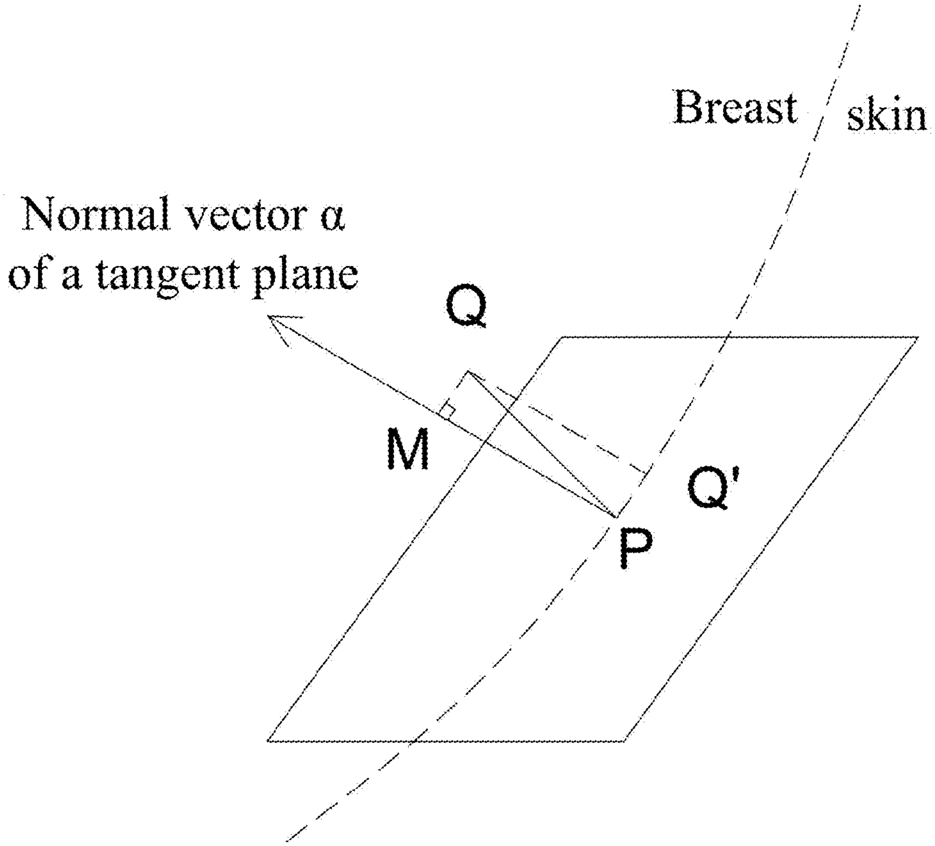
FIG. 7 illustrates a mathematical principle of a mask map according to an embodiment of the present disclosure.

As shown in FIG. 7, P is a point on the edge surface of the breast skin. When there is a small distance between points on the edge surface of the breast skin, the outer surface of the breast near each point is a plane orthogonal to a gradient direction of a signal value of a current point. Therefore, a distance QQ' from a point Q to the edge surface of the breast skin is equal to a projection PM of a distance between the point Q and the point P in the gradient direction α. Eliminating the breast skin region means eliminating points with a distance from the edge surface of the breast skin less than or equal to K, which is equivalent to eliminating, within a small neighborhood of a point on the edge surface of the skin, points whose distance from the point on the edge surface of the skin has a projection in the gradient direction less than or equal to K.

A thickness of the breast skin region is set to K, and the mask map is made based on the points on the edge surface of the breast skin to mark the breast skin region to be eliminated, with a mask calculation formula as follows:

$$y = \frac{\max(\kappa - d, 0)}{\kappa}, \tag{5}$$

where y is a calculated signal value of the mask map, and d represents a distance from a point to the edge surface of the breast skin.

Figure 8:
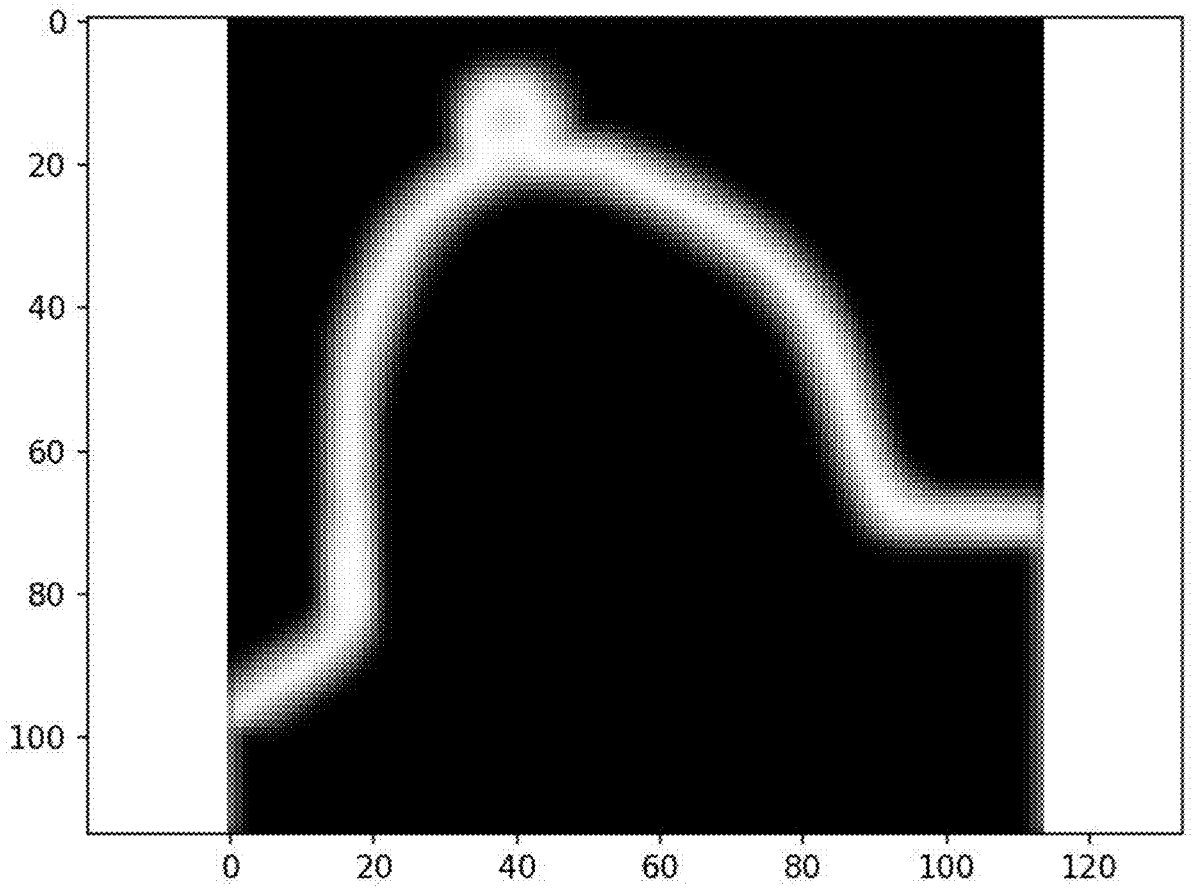
FIG. 8 is a made right breast mask map according to an embodiment of the present disclosure.

As shown in FIG. 8, in the mask map, y corresponding to the points on the edge surface of the breast skin is 1, and points at other positions linearly attenuates to 0 with the distance d.

Step 3.4: Remove the breast skin region in the three-dimensional image by means of the mask map obtained in step 3.3.

The gradient image of the breast is multiplied by an elimination coefficient to remove the breast skin region in the three-dimensional image. The elimination coefficient is calculated as follows:

$$\beta = 1 - y, \tag{6}$$

where y is a signal value in the mask map.

Step 4: Process, by means of an optimized three-dimensional non-maximum suppression algorithm, the three-dimensional image with the breast skin region removed, so as to make a contour of a mammary gland tissue clearer.

Figure 9:
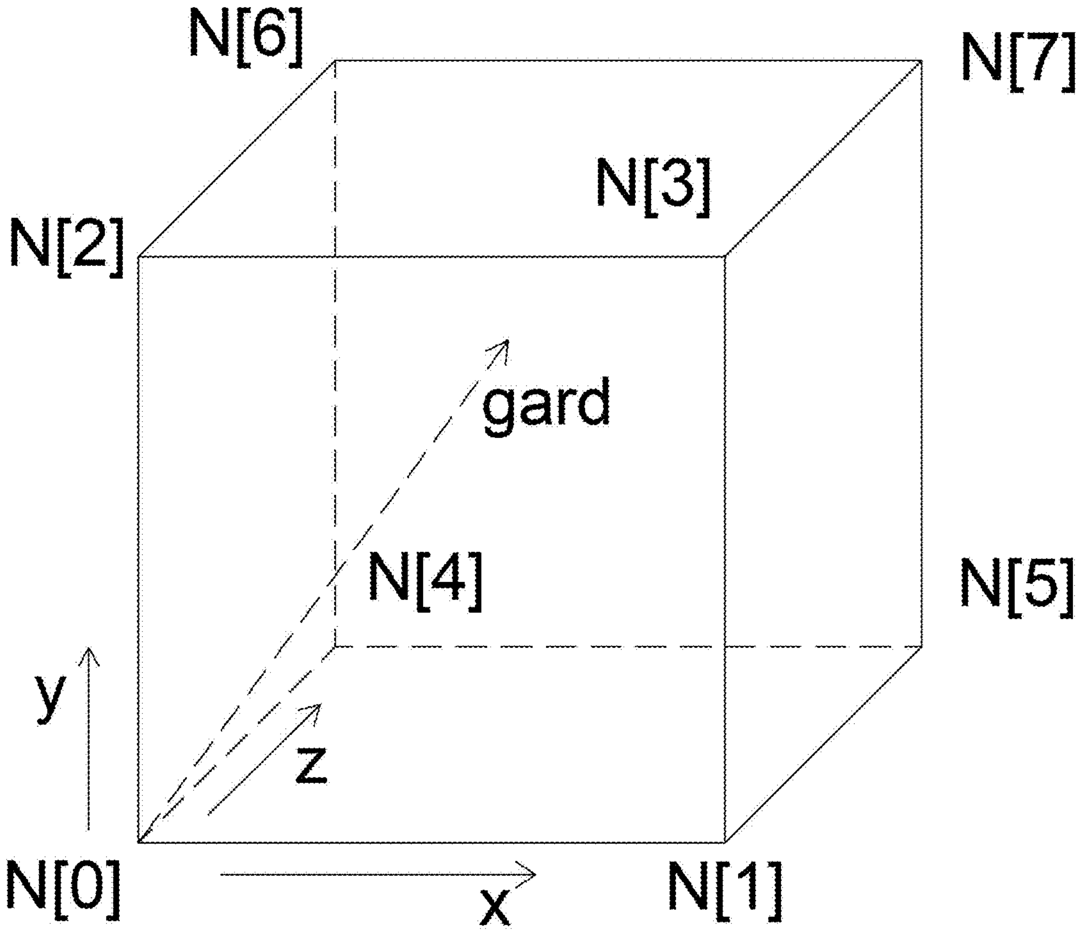
FIG. 9 illustrates an interpolation demonstration of a three-dimensional non-maximum suppression algorithm according to an embodiment of the present disclosure.

Given one voxel point and one gradient direction, the voxel point is denoted as $N_0$, and 7 nearest neighboring voxels ($N_1$ to $N_7$) pointed by the gradient direction form a 2×2×2 matrix. As shown in FIG. 9, each N represents one voxel point. The optimized three-dimensional non-maximum suppression algorithm is calculated by using the following method:

$$U_0 = N_0; \tag{7}$$

$$U_1 = N_1 - U_0; \tag{8}$$

$$U_2 = N_2 - U_0; \tag{9}$$

$$U_3 = N_3 - N_1 - U_2; \tag{10}$$

$$U_4 = N_4 - U_0; \tag{11}$$

$$U_5 = N_5 - N_1 - U_4; \tag{12}$$

$$U_6 = N_6 - N_2 - U_4; \tag{13}$$

$$U_7 = N_7 - N_3 - N_5 + N_1 - U_6; \text{ and} \tag{14}$$

$$R = U_0 + dz \times U_1 + dy(U_2 + dz \times U_3) + dx(U_4 + dz \times U_5) + + dy(U_6 + dz \times U_7), \tag{15}$$

where $N_0$ to $N_7$ represent voxel values corresponding to 8 octants, dx, dy, and dz are partial derivatives in three directions, and $U_0$ to $U_7$ represent intermediate variables.

Figure 10:
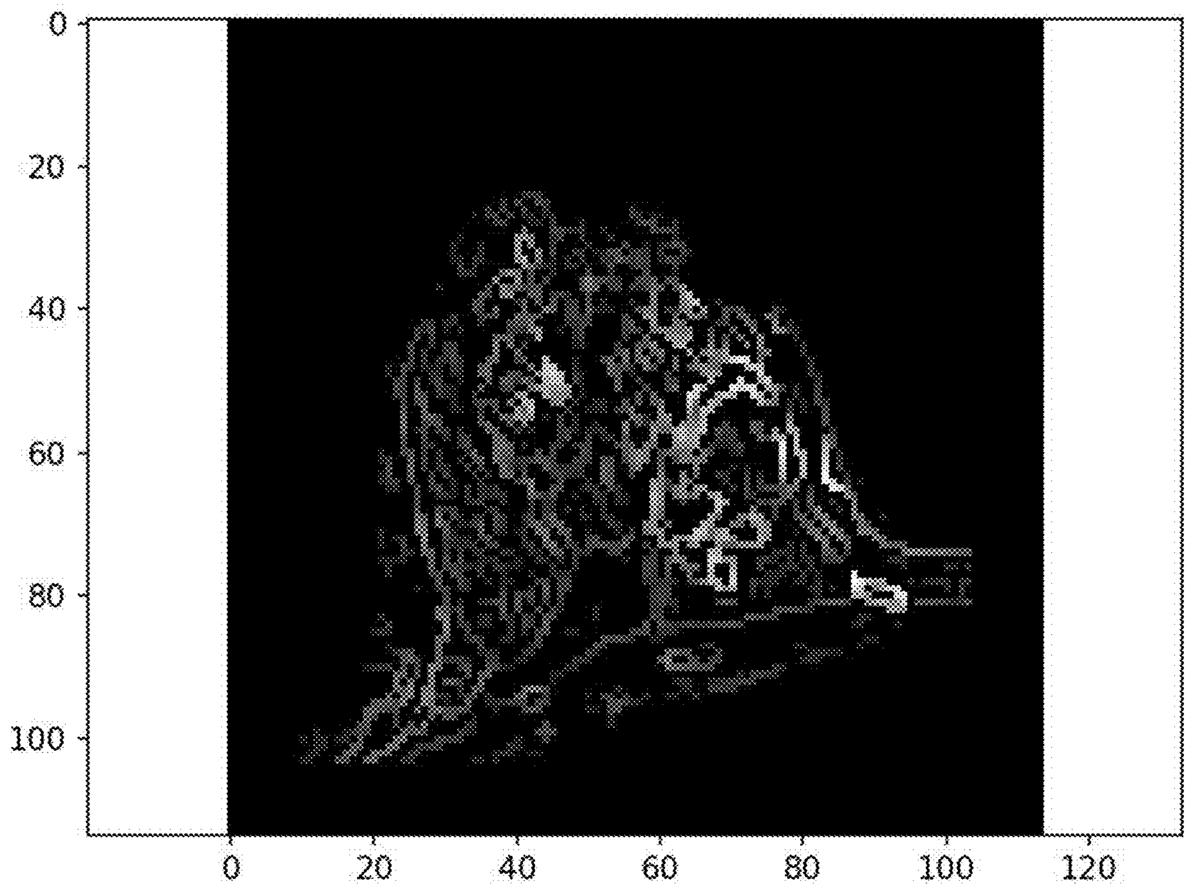
FIG. 10 illustrates a contour of a mammary gland tissue obtained by means of an optimized three-dimensional non-maximum suppression algorithm according to an embodiment of the present disclosure.

A first interpolation $R_1$ is calculated according to the voxel point gradient obtained in step 3.2, then the gradient direction is reversed to select 7 nearest neighboring voxels, a second interpolation $R_2$ is calculated according to formulas (7)-(15), and if the gradient value of the voxel point is greater than $R_1$ and $R_2$, the voxel point is kept, otherwise the voxel value of the voxel point is set to 0. As shown in FIG. 10, by means of the optimized three-dimensional non-maximum suppression algorithm, the contour is clearer while interference is removed.

Step 5: Implement, in six directions including positive and negative directions of an X-axis, positive and negative directions of a Y-axis, and positive and negative directions of a Z-axis, the probe algorithm on the three-dimensional image subjected to non-maximum suppression, record all detected edge points to obtain a complete three-dimensional contour of the mammary gland, fill the mammary gland region according to the contour of the mammary gland, and calculate a total number of voxels occupied by the filling to obtain a voxel volume of the mammary gland structure.

In an example in which a probe extends in the positive direction of the Y-axis, samples are taken at intervals in an XZ plane. For each group of X and Z, a value of Y traverses voxel values one by one in an ascending order (which is equivalent to extending out the probe from a left arm to a right arm), and a first voxel point whose voxel value exceeds a preset threshold γ is marked and recorded. Therefore, a two-dimensional array in the XZ plane can be obtained, and a first Y coordinate of a position of each element that exceeds the threshold γ is recorded. The probe extends out in five directions including the positive and negative directions of the X-axis, the negative direction of the Y-axis, and the positive and negative direction of the Z-axis in the same operation method, and all detected edge points are recorded to obtain the complete three-dimensional contour of the mammary gland. In this embodiment, the value of Y is 20, and a sampling interval in the YZ, XZ and XY planes is 0 The mammary gland region is filled according to the contour of the mammary gland, and the total number of voxels occupied by the filling is calculated to obtain the voxel volume of the mammary gland structure.

Step 6: Calculate a final mammary gland volume according to the voxel volume calculated in step 5 and a voxel spacing in DICOM data.

Embodiment 2

Based on the same inventive concept, the present disclosure further provides a system for automatically estimating a mammary gland volume based on a mammary gland MRI image, including a processor and a memory, where the memory is configured to store program instructions, and the processor is configured to invoke the program instructions in the memory to perform the method for automatically estimating a mammary gland volume based on a mammary gland MRI image described above.

During specific implementation, the method proposed in the technical solutions of the present disclosure can be automatically run by those skilled in the art by using a computer software technology, and system apparatuses for implementing the method, such as a computer-readable storage medium for storing corresponding computer programs of the technical solutions of the present disclosure and a computer device for running the corresponding computer programs, should also fall within the protection scope of the present disclosure.

The specific embodiments described herein are merely intended to illustrate the spirit of the present disclosure by way of example. A person skilled in the technical field to which the present disclosure belongs may make various modifications or supplements on the described specific embodiments or substitute them in a similar way, without departing from the spirit of the present disclosure or exceeding the scope defined by the appended claims.

What is claimed is:

1. A method for automatically estimating a mammary gland volume based on a mammary gland magnetic resonance imaging (MRI) image, comprising the following steps:

step 1: reading three-dimensional image data of a chest MRI image in digital imaging and communications in medicine (DICOM) format;

step 2: cutting the three-dimensional chest MRI image according to prior knowledge to extract a left chest region and a right chest region, and performing Gaussian blur processing on a three-dimensional image of a single breast;

step 3: removing a breast skin region in the three-dimensional image of the breast by means of an image processing algorithm;

wherein step 3 comprises step 3.1 to step 3.4:

step 3.1: marking points on an edge of breast skin by means of a search algorithm;

step 3.2: calculating partial derivatives of each three-dimensional image of left and right breasts in an X-axis direction, a Y-axis direction, and a Z-axis direction by means of a difference operator, and obtaining a gradient magnitude and direction of a position of each voxel in the three-dimensional image;

step 3.3: making a mask map based on the points on an edge surface of the breast skin detected in step 3.1, and marking the breast skin region to be eliminated; and step 3.4: removing, based on a gradient image obtained in step 3.2, the breast skin region in the three-dimensional image by means of the mask map obtained in step 3.3;

step 4: processing, by means of an optimized three-dimensional non-maximum suppression algorithm, the three-dimensional image with the breast skin region removed, so as to make a contour of a mammary gland tissue clearer;

step 5: implementing, in six directions comprising positive and negative directions of an X-axis, positive and negative directions of a Y-axis, and positive and negative directions of a Z-axis, the search algorithm on the three-dimensional image subjected to non-maximum suppression, recording all detected edge points to obtain a complete three-dimensional contour of the mammary gland, filling the mammary gland region according to the contour of the mammary gland, and calculating a total number of voxels occupied by the filling to obtain a voxel volume of the mammary gland structure; and step 6: calculating a final mammary gland volume according to the voxel volume calculated in step 5 and a voxel spacing.

2. The method for automatically estimating a mammary gland volume based on a mammary gland MRI image according to claim 1, wherein step 1 further comprises reading, from a chest MRI image set, a chest MRI image data storing three-dimensional images formed by MRI signals in a form of a three-dimensional array, each array element representing one voxel, converting the chest MRI image data into a python array format for storage, and recording a spacing between voxels in three directions, wherein the X-axis is directed from the front to the back of a body, the Y-axis is directed from a left arm to a right arm, and the Z-axis is directed from the top of a head to soles of feet.

3. The method for automatically estimating a mammary gland volume based on a mammary gland MRI image according to claim 1, wherein in step 2, according to prior knowledge on approximate positions of left and right chests in a chest MRI image, the three-dimensional MRI image is cut to extract the left chest region and the right chest region, the right chest region is horizontally flipped according to symmetry of breasts, signals of other organs unrelated to the breasts in the image are cut out to obtain a complete mammary gland region, and the Gaussian blur processing is performed on each three-dimensional image of the left and right breasts obtained through cutting, to eliminate an influence of MRI noise.

4. The method for automatically estimating a mammary gland volume based on a mammary gland MRI image according to claim 1, wherein in step 3.1, samples are taken at intervals in a YZ plane for a three-dimensional image of a single breast subjected to the Gaussian blur processing; for each group of Y and Z, a value of X traverses voxel values one by one in an ascending order, and a first voxel point whose voxel value exceeds a preset threshold d is marked and recorded, thus obtaining a two-dimensional array in the YZ plane, a first X coordinate of a position of each element that exceeds the threshold δ is recorded, and the marked voxel points are points on the edge surface of the breast skin.

5. The method for automatically estimating a mammary gland volume based on a mammary gland MRI image according to claim 1, wherein in step 3.2, partial derivative three-dimensional images dx, dy, and dz in the X-axis direction, the Y-axis direction, and the Z-axis direction are first obtained by means of the difference operator from the three-dimensional image of a single breast subjected to the Gaussian blur processing, and then a gradient numerical three-dimensional image is calculated from the three partial derivative images; the difference operator is set as a three-dimensional matrix in which three neighboring voxels in a corresponding direction are −1, 0, and 1, respectively, and the rest values are all 0, and the difference operator of the X-axis, the Y-axis and the Z-axis is expressed as follows:

$$\left(\begin{pmatrix}0&0&0\\0&0&0\\0&0&0\end{pmatrix}\begin{pmatrix}0&0&0\\1&0&-1\\0&0&0\end{pmatrix}\begin{pmatrix}0&0&0\\0&0&0\\0&0&0\end{pmatrix}\right); \quad (1)$$

$$\left(\begin{pmatrix}0&0&0\\0&0&0\\0&0&0\end{pmatrix}\begin{pmatrix}0&1&0\\0&0&0\\0&-1&0\end{pmatrix}\begin{pmatrix}0&0&0\\0&0&0\\0&0&0\end{pmatrix}\right); \text{ and} \quad (2)$$

$$\left(\begin{pmatrix}0&0&0\\0&1&0\\0&0&0\end{pmatrix}\begin{pmatrix}0&0&0\\0&0&0\\0&0&0\end{pmatrix}\begin{pmatrix}0&0&0\\0&-1&0\\0&0&0\end{pmatrix}\right); \quad (3)$$

the gradient numerical three-dimensional image is calculated from the three partial derivative images, and a gradient $\mathrm{Grad}_{i,j,k}$ of a point at a coordinate (i,j,k) is calculated as follows:

$$Grad_{i,j,k} = \sqrt{(A_{i+1,j,k}-A_{i-1,j,k})^2+(A_{i,j+1,k}-A_{i,j-1,k})^2+(A_{i,j,k+1}-A_{i,j,k-1})^2} = \sqrt{dx_{i,j,k}^2+dy_{i,j,k}^2+dz_{i,j,k}^2}, \quad (4)$$

wherein A represents a three-dimensional array of the MRI image, i, j, and k represent coordinates, and dx, dy, and dz represent three partial derivative three-dimensional arrays obtained by allowing the difference operator to act on A; and a vector that normalizes three partial derivatives is a direction unit vector of the gradient, and a gradient direction of a position of each voxel marks a direction in which signals increase and decrease fastest, and is orthogonal to a signal equipotential surface of the voxel.

6. The method for automatically estimating a mammary gland volume based on a mammary gland MRI image according to claim 1, wherein in step 3.3, a thickness of the breast skin region is set to κ, and the mask map is made based on the points on the edge surface of the breast skin to mark the breast skin region to be eliminated, with a mask calculation formula as follows:

$$y = \frac{\max(\kappa - d, 0)}{\kappa}, \quad (5)$$

wherein y is a calculated signal value of the mask map, and d represents a distance from a point to the edge surface of the breast skin; and in the mask map, y corresponding to the points on the edge surface of the breast skin is 1, and points at other positions linearly attenuate to 0 with the distance d.

7. The method for automatically estimating a mammary gland volume based on a mammary gland MRI image according to claim 6, wherein in step 3.4, the gradient image of the breast is multiplied by an elimination coefficient β to remove the breast skin region in the three-dimensional image; and the elimination coefficient is calculated as follows:

$$\beta = 1 - y, \quad (6)$$

wherein y is a signal value in the mask map.

8. The method for automatically estimating a mammary gland volume based on a mammary gland MRI image according to claim 1, wherein in step 4, the optimized three-dimensional non-maximum suppression algorithm is calculated by using the following method:

$$U_0 = N_0; \quad (7)$$

$$U_1 = N_1 - U_0; \quad (8)$$

$$U_2 = N_2 - U_0; \quad (9)$$

$$U_3 = N_3 - N_1 - U_2; \quad (10)$$

$$U_4 = N_4 - U_0; \quad (11)$$

$$U_5 = N_5 - N_1 - U_4; \quad (12)$$

$$U_6 = N_6 - N_2 - U_4; \quad (13)$$

$$U_7 = N_7 - N_3 - N_5 + N_1 - U_6; \text{ and} \quad (14)$$

$$R = U_0 + dz\times U_1 + dy(U_2 + dz\times U_3) + dx(U_4 + dz\times U_5) ++ dy(U_6 + dz\times U_7), \quad (15)$$

wherein $N_0$ to $N_7$ represent voxel values corresponding to 8 octants, dx, dy, and dz are partial derivatives in three directions, and $U_0$ to $U_7$ represent intermediate variables; and a first interpolation $R_1$ is calculated according to the voxel point gradient obtained in step 3.2, then the gradient direction is reversed to select 7 nearest neighboring voxels, a second interpolation $R_2$ is calculated according to formulas (7)-(15), and if the gradient value of the voxel point $N_0$ is greater than $R_1$ and $R_2$, the voxel point is kept, otherwise the voxel value of the voxel point is set to 0.

9. The method for automatically estimating a mammary gland volume based on a mammary gland MRI image according to claim 1, wherein in step 5, the search algorithm is implemented in the positive direction of the Y-axis to take samples at intervals in an XZ plane; for each group of X and Z, a value of Y traverses voxel values one by one in an ascending order, and a first voxel point whose voxel value exceeds a preset threshold γ is marked and recorded, thus obtaining a two-dimensional array in the XZ plane, and a first Y coordinate at a position of each element that exceeds the threshold γ is recorded; operations of implementing the search algorithm in five directions comprising the positive and negative directions of the X-axis, the negative direction of the Y-axis, and the positive and negative direction of the Z-axis are similar to the above operation, edge points detected in all directions are recorded to obtain the complete three-dimensional contour of the mammary gland, the mammary gland region is filled according to the contour of the mammary gland, and the total number of voxels occupied by the filling is calculated to obtain the voxel volume of the mammary gland structure.

10. A system for automatically estimating a mammary gland volume based on a mammary gland MRI image, comprising a processor and a memory, wherein the memory is configured to store program instructions, and the processor is configured to invoke the program instructions in the memory to perform the method for automatically estimating a mammary gland volume based on a mammary gland MRI image according to claim 1.

11. The system according to claim 10, wherein step 1 further comprises reading, from a chest MRI image set, a chest MRI image data storing three-dimensional images formed by MRI signals in a form of a three-dimensional array, each array element representing one voxel, converting the chest MRI image data into a python array format for storage, and recording a spacing between voxels in three directions, wherein the X-axis is directed from the front to the back of a body, the Y-axis is directed from a left arm to a right arm, and the Z-axis is directed from the top of a head to soles of feet.

12. The system according to claim 10, wherein in step 2, according to prior knowledge on approximate positions of left and right chests in a chest MRI image, the three-dimensional MRI image is cut to extract the left chest region and the right chest region, the right chest region is horizontally flipped according to symmetry of breasts, signals of other organs unrelated to the breasts in the image are cut out to obtain a complete mammary gland region, and the Gaussian blur processing is performed on each three-dimensional image of the left and right breasts obtained through cutting, to eliminate an influence of MRI noise.

13. The system according to claim 10, wherein in step 3.1, samples are taken at intervals in a YZ plane for a three-dimensional image of a single breast subjected to the Gaussian blur processing; for each group of Y and Z, a value of X traverses voxel values one by one in an ascending order, and a first voxel point whose voxel value exceeds a preset threshold d is marked and recorded, thus obtaining a two-dimensional array in the YZ plane, a first X coordinate of a position of each element that exceeds the threshold δ is recorded, and the marked voxel points are points on the edge surface of the breast skin.

14. The system according to claim 10, wherein in step 3.2, partial derivative three-dimensional images dx, dy, and dz in the X-axis direction, the Y-axis direction, and the Z-axis direction are first obtained by means of the difference operator from the three-dimensional image of a single breast subjected to the Gaussian blur processing, and then a gradient numerical three-dimensional image is calculated from the three partial derivative images; the difference operator is set as a three-dimensional matrix in which three neighboring voxels in a corresponding direction are −1, 0, and 1, respectively, and the rest values are all 0, and the difference operator of the X-axis, the Y-axis and the Z-axis is expressed as follows:

$$\left(\begin{pmatrix}0&0&0\\0&0&0\\0&0&0\end{pmatrix}\begin{pmatrix}0&0&0\\1&0&-1\\0&0&0\end{pmatrix}\begin{pmatrix}0&0&0\\0&0&0\\0&0&0\end{pmatrix}\right); \quad (1)$$

$$\left(\begin{pmatrix}0&0&0\\0&0&0\\0&0&0\end{pmatrix}\begin{pmatrix}0&1&0\\0&0&0\\0&-1&0\end{pmatrix}\begin{pmatrix}0&0&0\\0&0&0\\0&0&0\end{pmatrix}\right); \text{and} \quad (2)$$

$$\left(\begin{pmatrix}0&0&0\\0&1&0\\0&0&0\end{pmatrix}\begin{pmatrix}0&0&0\\0&0&0\\0&0&0\end{pmatrix}\begin{pmatrix}0&0&0\\0&-1&0\\0&0&0\end{pmatrix}\right); \quad (3)$$

the gradient numerical three-dimensional image is calculated from the three partial derivative images, and a gradient $\text{Grad}_{i,j,k}$ of a point at a coordinate (i,j,k) is calculated as follows:

$$Grad_{i,j,k} = \sqrt{(A_{i+1,j,k}-A_{i-1,j,k})^2+(A_{i,j+1,k}-A_{i,j-1,k})^2+(A_{i,j,k+1}-A_{i,j,k-1})^2} = \sqrt{dx_{i,j,k}^2+dy_{i,j,k}^2+dz_{i,j,k}^2}, \quad (4)$$

wherein A represents a three-dimensional array of the MRI image, i, j, and k represent coordinates, and dx, dy, and dz represent three partial derivative three-dimensional arrays obtained by allowing the difference operator to act on A; and a vector that normalizes three partial derivatives is a direction unit vector of the gradient, and a gradient direction of a position of each voxel marks a direction in which signals increase and decrease fastest, and is orthogonal to a signal equipotential surface of the voxel.

15. The system according to claim 10, wherein in step 3.3, a thickness of the breast skin region is set to κ, and the mask map is made based on the points on the edge surface of the breast skin to mark the breast skin region to be eliminated, with a mask calculation formula as follows:

$$y = \frac{\max(\kappa - d, 0)}{\kappa}, \quad (5)$$

wherein y is a calculated signal value of the mask map, and d represents a distance from a point to the edge surface of the breast skin; and in the mask map, y corresponding to the points on the edge surface of the breast skin is 1, and points at other positions linearly attenuate to 0 with the distance d.

16. The system according to claim 15, wherein in step 3.4, the gradient image of the breast is multiplied by an elimination coefficient β to remove the breast skin region in the three-dimensional image; and the elimination coefficient is calculated as follows:

$$\beta = 1 - y, \quad (6)$$

wherein y is a signal value in the mask map.

17. The system according to claim 10, wherein in step 4, the optimized three-dimensional non-maximum suppression algorithm is calculated by using the following method:

$$U_0 = N_0; \quad (7)$$

$$U_1 = N_1 - U_0; \quad (8)$$

$$U_2 = N_2 - U_0; \quad (9)$$

$$U_3 = N_3 - N_1 - U_2; \quad (10)$$

$$U_4 = N_4 - U_0; \quad (11)$$

$$U_5 = N_5 - N_1 - U_4; \quad (12)$$

$$U_6 = N_6 - N_2 - U_4; \quad (13)$$

$$U_7 = N_7 - N_3 - N_5 + N_1 - U_6; \text{ and} \quad (14)$$

$$R = U_0 + dz \times U_1 + dy(U_2 + dz \times U_3) + dx(U_4 + dz \times U_5) ++ dy(U_6 + dz \times U_7), \quad (15)$$

wherein $N_0$ to $N_7$ represent voxel values corresponding to 8 octants, dx, dy, and dz are partial derivatives in three directions, and $U_0$ to $U_7$ represent intermediate variables; and a first interpolation $R_1$ is calculated according to the voxel point gradient obtained in step 3.2, then the gradient direction is reversed to select 7 nearest neighboring voxels, a second interpolation $R_2$ is calculated according to formulas (7)-(15), and if the gradient value of the voxel point $N_0$ is greater than $R_1$ and $R_2$, the voxel point is kept, otherwise the voxel value the voxel point is set to 0.

18. The system according to claim 10, wherein in step 5, the search algorithm is implemented in the positive direction of the Y-axis to take samples at intervals in an XZ plane; for each group of X and Z, a value of Y traverses voxel values one by one in an ascending order, and a first voxel point whose voxel value exceeds a preset threshold γ is marked and recorded, thus obtaining a two-dimensional array in the XZ plane, and a first Y coordinate at a position of each element that exceeds the threshold γ is recorded; operations of implementing the search algorithm in five directions comprising the positive and negative directions of the X-axis, the negative direction of the Y-axis, and the positive and negative direction of the Z-axis are similar to the above operation, edge points detected in all directions are recorded to obtain the complete three-dimensional contour of the mammary gland, the mammary gland region is filled according to the contour of the mammary gland, and the total number of voxels occupied by the filling is calculated to obtain the voxel volume of the mammary gland structure.

* * * * *